(12) United States Patent
Lee et al.

(10) Patent No.: US 10,517,567 B2
(45) Date of Patent: Dec. 31, 2019

(54) DOCKING STATION FOR AN ULTRASOUND PROBE

(71) Applicant: General Electric Company, Schenectady, NY (US)

(72) Inventors: Warren Lee, Niskayuna, NY (US); Naveenan Thiagarajan, Schenectady, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 16/243,823

(22) Filed: Jan. 9, 2019

(65) Prior Publication Data

US 2019/0142378 A1 May 16, 2019

Related U.S. Application Data

(63) Continuation of application No. 14/973,739, filed on Dec. 18, 2015, now Pat. No. 10,206,658.

(51) Int. Cl.
| | |
|---|---|
| *H01M 10/46* | (2006.01) |
| *A61B 8/00* | (2006.01) |
| *H02J 7/00* | (2006.01) |
| *H02J 7/02* | (2016.01) |
| *H02J 50/10* | (2016.01) |

(52) U.S. Cl.
CPC ............ *A61B 8/4433* (2013.01); *A61B 8/546* (2013.01); *A61B 8/56* (2013.01); *H02J 7/0027* (2013.01); *H02J 7/0044* (2013.01); *H02J 7/025* (2013.01); *H02J 50/10* (2016.02)

(58) Field of Classification Search
CPC ............... H02J 7/355; H02J 7/025; H02J 5/05
USPC ................. 320/107, 108, 114, 115; 700/300; 361/676, 678, 679.01
See application file for complete search history.

(56) References Cited

U.S. PATENT DOCUMENTS

| 10,206,658 B2 * | 2/2019 | Lee | ...................... A61B 8/546 |
| 2008/0146922 A1 * | 6/2008 | Steins | ..................... A61B 8/546 600/437 |

FOREIGN PATENT DOCUMENTS

| CN | 101584097 A | 11/2009 |
| CN | 104471508 A | 3/2015 |

OTHER PUBLICATIONS

Office Action, corresponding CN Patent Application No. 201611168788.2, dated Jun. 25, 2019, 13 pages (English translation not available).

* cited by examiner

*Primary Examiner* — Edward Tso

(57) ABSTRACT

A docking station for electrically charging and managing a thermal condition of an ultrasound probe is presented. The docking station includes a first charging unit magnetically coupled to an induction unit of the ultrasound probe and configured to charge at least one battery in the ultrasound probe. Further, the docking station includes a first cooling unit thermally coupled to a thermal unit of the ultrasound probe and configured to dissipate heat from the ultrasound probe.

20 Claims, 5 Drawing Sheets

DOCKING STATION FOR AN ULTRASOUND PROBE

CROSS-REFERENCE TO RELATED APPLICATIONS

The present application is a continuation of U.S. patent application Ser. No. 14/973,739, filed on Dec. 18, 2015 which is incorporated herein by reference in its entirety.

BACKGROUND

Embodiments of the present specification relate generally to an ultrasound probe, and more particularly to a docking station for electrically charging and managing a thermal condition of the ultrasound probe.

Medical diagnostic ultrasound is an imaging modality that employs ultrasound waves to probe acoustic properties of biological tissues and produces corresponding images. Particularly, ultrasound systems are used to provide an accurate visualization of muscles, tendons, and other internal organs to assess their size, structure, movement, and/or any pathological conditions using near real-time images. Moreover, owing to the ability to image the underlying tissues without the use of ionizing radiation, ultrasound systems find extensive use in angiography and prenatal scanning.

Typically, ultrasound systems employ an ultrasound probe that houses components, such as an internal battery, beamforming electronics, and transmitter and receiver circuitry for transmitting and receiving ultrasound signals from a target volume in a subject or a patient. Further, these ultrasound signals are processed to obtain a quality image of the subject. However, during operation, the components of the ultrasound probe may generate heat, which in turn may affect or limit the operation of the probe. Also, as the internal battery in the probe is used for supplying electrical power to other components in the probe, electrical charge in the battery may be drained frequently. Thus, it is desirable to charge the battery of the probe while simultaneously managing a thermal condition of the probe.

In conventional ultrasound systems, the thermal condition of the ultrasound probe is managed by increasing the surface area of the ultrasound probe to absorb or dissipate the heat generated in the probe. However, this increase in the size of the ultrasound probe may have repercussions on the ergonomics and/or hygiene aspects of the ultrasound probe. Also, the presently available techniques entail separately charging the internal battery in the ultrasound probe via use of a wired connector and an external power supply.

BRIEF DESCRIPTION

In accordance with aspects of the present specification, a docking station for electrically charging and managing a thermal condition of an ultrasound probe is presented. The docking station includes a first charging unit magnetically coupled to an induction unit of the ultrasound probe and configured to charge at least one battery in the ultrasound probe. Further, the docking station includes a first cooling unit thermally coupled to a thermal unit of the ultrasound probe and configured to dissipate heat from the ultrasound probe.

In accordance with a further aspect of the present specification, a method for electrically charging and managing a thermal condition of an ultrasound probe is presented. The method includes magnetically coupling a first charging unit of a docking station to an induction unit of an ultrasound probe to charge at least one battery in the ultrasound probe. Moreover, the method includes thermally coupling a first cooling unit of the docking station to a thermal unit of the ultrasound probe to dissipate heat from the ultrasound probe.

In accordance with another aspect of the present specification, an ultrasound system is presented. The ultrasound system includes an ultrasound probe including a housing and an induction unit coupled to at least one battery. Further, the ultrasound probe includes a thermal unit configured to absorb heat generated in the ultrasound probe. In addition, the ultrasound system includes a docking station including a first charging unit magnetically coupled to the induction unit of the ultrasound probe and configured to charge the at least one battery through the induction unit. Also, the docking station includes a first cooling unit thermally coupled to the thermal unit of the ultrasound probe and configured to dissipate the absorbed heat from the thermal unit of the ultrasound probe.

DRAWINGS

These and other features, aspects, and advantages of the present invention will become better understood when the following detailed description is read with reference to the accompanying drawings in which like characters represent like parts throughout the drawings, wherein.

Figure 1:
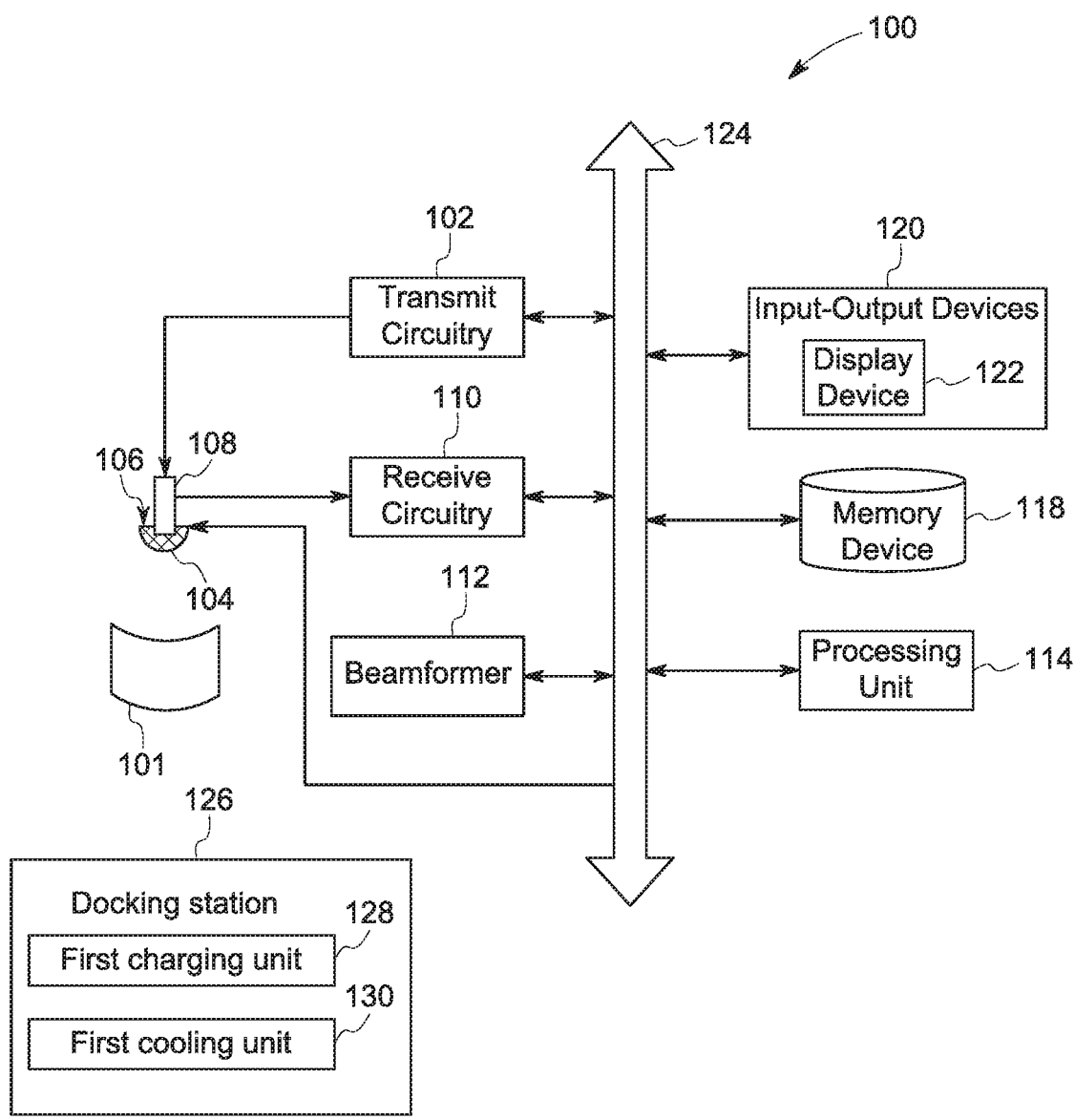
FIG. 1 is a diagrammatical representation of an ultrasound system for imaging a target volume in a subject, in accordance with aspects of the present specification.
Figure 4:
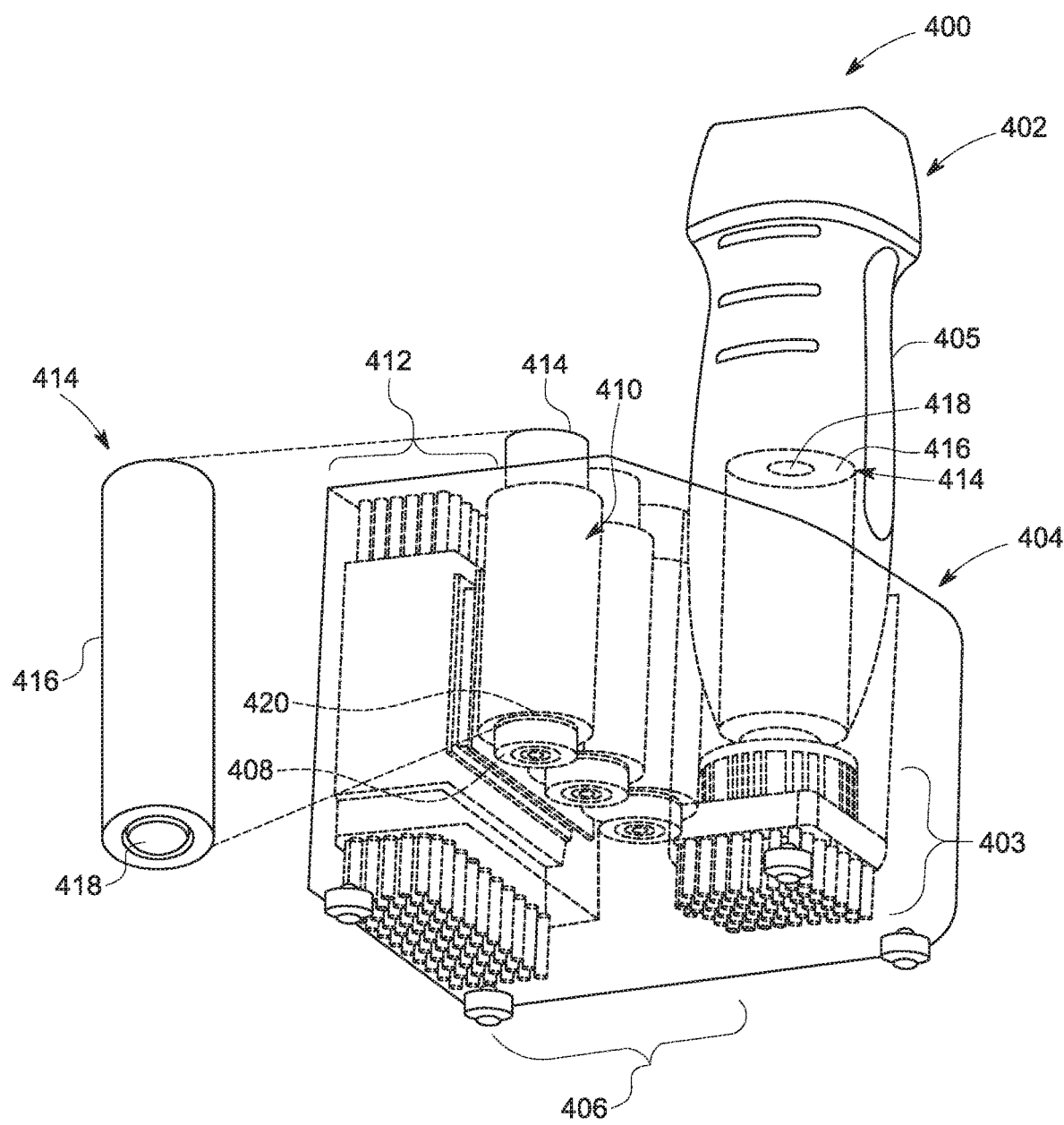
Figure 5:
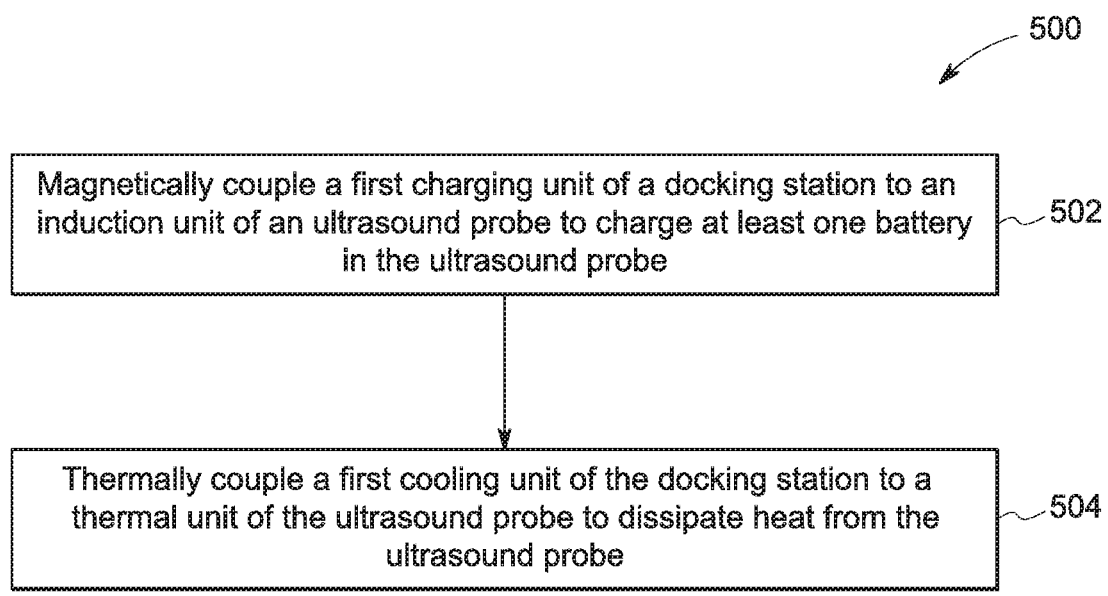

FIG. 4 is a diagrammatical representation of yet another embodiment of charging an ultrasound probe via use of a docking station for electrically charging and thermally cooling the ultrasound probe, in accordance with aspects of the present specification; and FIG. 5 is a flow chart illustrating a method for electrically charging and managing a thermal condition of the ultrasound probe of FIG. 1, in accordance with aspects of the present specification.

DETAILED DESCRIPTION

As will be described in detail hereinafter, various embodiments of exemplary systems and methods for electrically charging and thermally cooling an ultrasound probe are presented. In particular, the systems and methods presented herein aid in electrically charging one or more batteries in the ultrasound probe while simultaneously dissipating heat generated in the ultrasound probe. By charging the batteries and cooling other components in the ultrasound probe, thermal condition and performance of the ultrasound probe may be significantly improved. Also, use of the exemplary systems and methods presented herein circumvent the need for increasing the size of the ultrasound probe to thermally cool or dissipate the heat generated in the ultrasound probe. This in turn enhances ergonomics and/or hygiene aspects of the ultrasound probe.

FIG. 1 illustrates an ultrasound system 100 for imaging a target volume 101 in a subject. In one embodiment, the ultrasound system 100 may be configured as a console system or a cart-based system. Alternatively, the ultrasound system 100 may be configured as a portable system, such as a hand-held, laptop-style and/or a smartphone-based system. For ease of description, the ultrasound system 100 is represented as a portable ultrasound system.

Further, in the present specification, the ultrasound system 100 is presented as being used to image the target volume 101 in biological tissues of interest. In one example, the target volume 101 may include cardiac tissues, liver tissues, breast tissues, prostate tissues, thyroid tissues, lymph nodes, vascular structures adipose tissue, muscular tissue, and/or blood cells. Alternatively, the system 100 may be employed for imaging non-biological materials such as manufactured parts, plastics, aerospace composites, and/or foreign objects within a body such as a catheter or a needle.

In certain embodiments, the system 100 includes transmit circuitry 102 that generates a pulsed waveform to drive a transducer array 104 of transducer elements 106 housed within a transducer probe 108. Particularly, the pulsed waveform drives the transducer array 104 of transducer elements 106 to emit ultrasonic pulses into the target volume 101. The transducer elements 106, for example, may include piezoelectric, piezoceramic, capacitive, and/or microfabricated crystals. At least a portion of the ultrasonic pulses generated by the transducer elements 106 is back-scattered from the target volume 101 to produce echoes that return to the transducer array 104 and are received by receive circuitry 110 for further processing. It may be noted that the terms "ultrasonic" and "ultrasound" may be used interchangeably in the following description.

Also, in the embodiment illustrated in FIG. 1, the receive circuitry 110 is coupled to a beamformer 112 that processes the received echoes and outputs corresponding radio frequency (RF) signals. Subsequently, a processing unit 114 receives and processes the RF signals in near real-time and/or offline mode. The processing unit 114 includes devices such as one or more general-purpose or application-specific processors, digital signal processors, microcomputers, microcontrollers, Application Specific Integrated Circuits (ASICs), Field Programmable Gate Arrays (FPGA), or other suitable devices in communication with other components of the system 100.

Moreover, in certain embodiments, the processing unit 114 also provides control and timing signals for configuring one or more imaging parameters for imaging the target volume 101 in the subject. Furthermore, in one embodiment, the processing unit 114 stores the delivery sequence, frequency, time delay, and/or beam intensity, for example, in a memory device 118 for use in imaging the target volume 101. The memory device 118 includes storage devices such as a random access memory, a read only memory, a disc drive, solid-state memory device, and/or a flash memory. In one embodiment, the processing unit 114 uses the stored information for configuring the transducer elements 106 to direct one or more groups of pulse sequences toward the target volume 101. Subsequently, the processing unit 114 tracks the displacements in the target volume 101 caused in response to the incident pulses to determine corresponding tissue characteristics. The displacements and tissues characteristics, thus determined, are stored in the memory device 118. The displacements and tissues characteristics may also be communicated to a medical practitioner, such as a radiologist, for further diagnosis.

In some embodiments, the processing unit 114 may be further coupled to one or more user input-output devices 120 for receiving commands and inputs from an operator, such as the medical practitioner. The input-output devices 120, for example, may include devices such as a keyboard, a touchscreen, a microphone, a mouse, a control panel, a display device 122, a foot switch, a hand switch, and/or a button. In one embodiment, the processing unit 114 processes the RF signal data to prepare image frames and to generate the requested medically relevant information based on user input. Particularly, the processing unit 114 may be configured to process the RF signal data to generate two-dimensional (2D) and/or three-dimensional (3D) datasets corresponding to different imaging modes.

Further, the processing unit 114 may be configured to reconstruct desired images from the 2D or 3D datasets. Subsequently, the processing unit 114 may be configured to display the desired images on the associated display device 122 that may be communicatively coupled to the processing unit 114. The display device 122, for example, may be a local device. Alternatively, in one embodiment, the display device 122 may be remotely located to allow a remotely located medical practitioner to access the reconstructed images and/or medically relevant information corresponding to the target volume 101 in the subject/patient. It may be noted that the various components of the ultrasound system 100 are communicatively coupled via a communication channel 124.

Moreover, in one embodiment, components such as the transmit and receive circuitries 102, 110 and the beamformer 112 may be included within the ultrasound probe 108. Further, these components 102, 110, 112 in the probe 108 may wirelessly communicate with other components 120, 118, 114 of the ultrasound system 100. Also, the ultrasound probe 108 may include an internal battery that is used for supplying electrical power to the one or more components 102, 110, 112 in the ultrasound probe 108. However, during operation of the ultrasound probe 108, these components 102, 110, 112 may generate heat in the probe 108, which in turn may affect or limit the operation of the probe 108. Also, as the internal battery in the probe 108 is used for supplying electrical power to the components 102, 110, 112 in the probe 108, electrical charge in the battery may be frequently discharged or drained.

In a conventional ultrasound system, the ultrasound probe is enlarged or the surface area of the ultrasound probe is increased to manage the thermal condition or absorb the heat generated in the probe. However, this increase in the size of the ultrasound probe may have repercussions on the ergonomics and/or hygiene aspects of the ultrasound probe. Also, the presently available techniques entail separately charging the internal battery in the ultrasound probe via use of a wired connector and an external power supply.

These shortcomings of the presently available systems may be circumvented via use of a docking station 126 in the ultrasound system 100. The docking station 126 is configured to electrically charge the internal battery of the ultrasound probe 108, while simultaneously managing the thermal condition of the probe 108. In one embodiment, the docking station 126 includes a first charging unit 128 and a first cooling unit 130. Further, when the probe 108 is coupled to the docking station 126, the first charging unit 128 may be magnetically coupled to an induction unit (see FIG. 2) of the ultrasound probe 108 and configured to charge the internal battery of the ultrasound probe 108. Concurrently, the first cooling unit 130 may be coupled to a thermal unit (see FIG. 2) of the ultrasound probe 108 and configured to dissipate heat from the ultrasound probe 108. It may be noted that the aspect of electrically charging and managing the thermal condition of the ultrasound probe 108 will be described in greater detail with reference to FIGS. 2-5. Thus, by employing the docking station 126 in the ultrasound system 100, the thermal condition of the ultrasound probe 108 and the electrical charge in the probe 108 may be managed without increasing the size and/or surface area of the probe 108.

Figure 2:
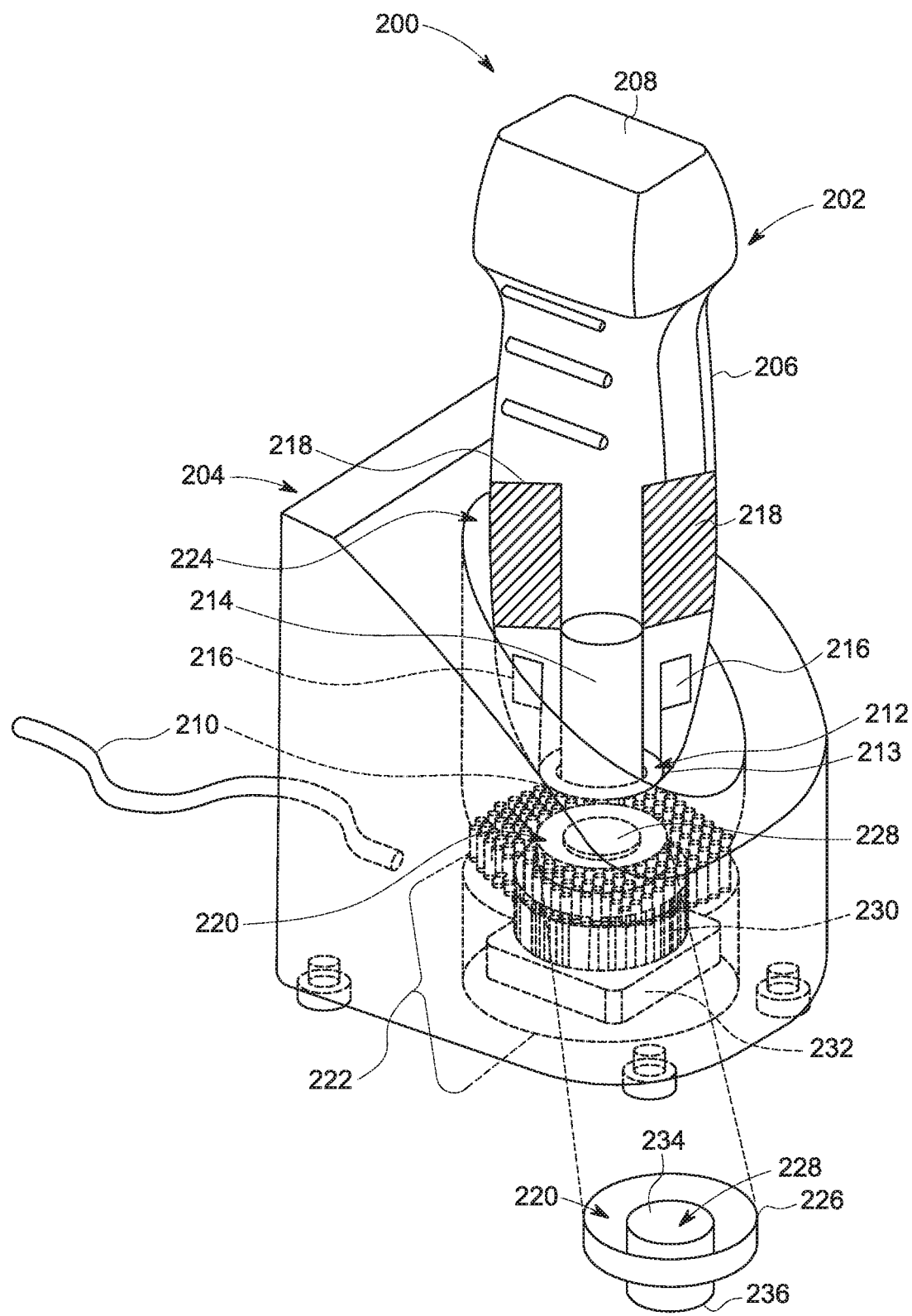
FIG. 2 is a diagrammatical representation of one embodiment of a docking station for electrically charging and thermally cooling an ultrasound probe, in accordance with aspects of the present specification.

Turning now to FIG. 2, a diagrammatical representation 200 of one embodiment of an exemplary docking station 204, in accordance with aspects of the present specification, is depicted. The docking station 204 may be configured to electrically charge an ultrasound probe 202 and concurrently manage a thermal condition of the ultrasound probe 202. The ultrasound probe 202 may be representative of one embodiment of the ultrasound probe 108 of FIG. 1. Also, the docking station 204 may be representative of one embodiment of the docking station 126 of FIG. 1. The ultrasound probe 202 and the docking station 204 are described with reference to the components of FIG. 1.

In a presently contemplated configuration, the ultrasound probe 202 includes a housing 206 having a top surface 208 and a bottom surface 210. It may be noted that the housing 206 may have one or more desired shapes depending upon a target volume 101 in a subject/patient being scanned. Further, the top surface 208 of the housing 206 may be a smooth closed surface that is disposed in contact with the subject being scanned. In one example, the top surface 208 may be positioned on surfaces, such as the chest, breast, and/or abdominal regions of the subject/patient being scanned. Also, when the ultrasound probe 202 is not used for scanning, the bottom surface 210 of the housing 206 may be brought in contact with the docking station 204 for electrically charging and/or managing the thermal condition of the probe 202.

In the embodiment of FIG. 2, the probe 202 includes an induction unit 212, a thermal unit 214, one or more batteries 216, and one or more thermal management units 218. The induction unit 212 may be referred to as a charging unit that is used to charge one or more batteries 216 in the probe 202. The one or more batteries 216 may be used for providing electrical power to other components in the probe 202. The thermal unit 214 may be referred to as a heat dissipating unit that is used to absorb heat generated in the probe 202. Further, the one or more thermal management units 218 may referred to as heat transferring units that are used to transfer the heat generated in the probe 202 to the thermal unit 214. In one example, the thermal management units 218 include at least one of a heat spreader and a heat pipe in the probe 202, which transfer the heat from other components in the probe 202 to the thermal unit 214.

In a presently contemplated configuration, the induction unit 212 may be electrically coupled to the batteries 216 and configured to electrically charge the batteries 216 in the probe 202. In one example, the induction unit 212 may include a first wireless induction charging ring 213 that is positioned along/about the bottom surface 210 of the housing 206. In one embodiment, the batteries 216 may be considered as a part of the induction unit 212.

Further, the thermal unit 214 may be thermally coupled to the one or more thermal management units 218 and configured to absorb heat generated in the probe 202. In one example, the thermal unit 214 may be a cylindrical cartridge, where a portion of the cylindrical cartridge is positioned within the first wireless induction charging ring 213, as depicted in FIG. 2. This cylindrical cartridge is configured to receive the heat from the thermal management units 218.

In another embodiment, the thermal unit 214 may include one or more phase change material (PCM) cartridges that are thermally coupled to the one or more thermal management units 218. Also, these PCM cartridges are used to absorb and store the heat generated in the probe 202. In one example, the PCM cartridges include materials, such as paraffin, fatty acids, oils, and salt hydrates that are capable of absorbing and storing the heat. In one embodiment, the PCM cartridges may include one or more materials that may melt or transition the phase of the materials while absorbing and storing the heat in the PCM cartridges. In one example, the melting point or phase transition temperature may be in a range from about 20 degree Celsius to about 50 degree Celsius. In another embodiment, the PCM cartridges may include internal heat transfer structures, such as, but not limited to, fins, heat pipes, and foams to enhance heat storage in the PCM cartridges. Also, the foams used in the PCM cartridges may be made of graphite, carbon, metal, and the like.

In one embodiment, the thermal unit 214 may be easily replaceable with a new thermal unit. In one example, the probe 202 may include a port at the bottom surface 210 of the housing 206 to facilitate removal of the thermal unit 214 from the probe 202. Further, the new thermal unit 214 may be inserted into the probe 202 via this port at the bottom surface 210 of the housing 206.

Furthermore, the induction unit 212 and the thermal unit 214 may be positioned in a concentric arrangement to form the bottom surface 210 of the housing 206. This arrangement aids in magnetically and thermally coupling the probe 202 to the docking station 204 when the probe 202 is positioned in the docking station 204.

Moreover, in one example, the docking station 204 may include a cavity 224 for receiving the probe 202. Furthermore, in one exemplary embodiment, the docking station 204 may include a first charging unit 220 and a first cooling unit 222. Further, the first charging unit 220 and the first cooling unit 222 are positioned within the cavity 224 of the docking station 204, as depicted in FIG. 2.

Further, the first charging unit 220 may be electrically coupled to the induction unit 212 of the probe 202 and configured to electrically charge the batteries 216 in the probe 202 via the induction unit 212. In one example, the first charging unit 220 may include a second wireless induction charging ring 226. The second wireless induction charging ring 226 aids in magnetically coupling the probe 202 to the docking station 204 when the probe 202 is positioned in the docking station 204. In particular, when the probe 202 is positioned in the docketing station 204, the second wireless induction charging ring 226 is magnetically coupled to the first wireless induction charging ring 213 of the induction unit 212.

Also, it may be noted that the first charging unit 220 may include other electronic components (not shown) that are used to electrically couple the first charging unit 220 to an external power source (not shown). Moreover, these electronic components may aid in supplying electrical power from the external power source to the second wireless induction charging ring 226 in the first charging unit 220. Further, the electrical power may be wirelessly transferred from the second wireless induction charging ring 226 to first wireless induction charging ring 213 of the induction unit 212 in the probe 202 to charge the batteries 216 in the probe 202.

In some embodiments, the docking station 204 may also provide a conventional method of charging the batteries 216. Particularly, the docking station 204 may include a socket coupled to the external power supply, and the probe 202 may include a wired cable coupled to the batteries 218 of the probe 202. Further, the wired cable of the probe 202 may be inserted into the socket of the docking station 204 to facilitate wired charging of the batteries 216.

In addition, the first cooling unit 222 may be thermally coupled to the thermal unit 214 of the probe 202 and configured to dissipate the heat from the probe 202. In one embodiment, the first cooling unit 222 includes a first thermoelectric cooler (TEC) 228, a first heat sink 230, and a first fan 232. The first TEC 228 is positioned on the first heat sink 230, while the first fan 232 is positioned below the first heat sink 230, as depicted in FIG. 2. Further, the first TEC 228 is thermally coupled to the thermal unit 214 of the probe 202 to absorb the heat stored in the thermal unit 214. In one example, the first TEC 228 may be positioned concentrically within respect to the second wireless induction charging ring 226, as depicted in FIG. 2. In another example, the first TEC 228 may be a solid state Peltier effect device that is capable of absorbing the heat from the thermal unit 214.

In the embodiment of FIG. 2, the first TEC 228 has a first surface 234 and a second surface 236. The first surface 234 may be configured as a cold top surface, while the second surface 236 may be configured as a hot bottom surface. Moreover, when the probe 202 is inserted into the docking station 204, the first surface 234 of the first TEC 228 may establish contact with the thermal unit 214 of the probe 202 to absorb the heat stored in the thermal unit 214. Further, the first heat sink 230 is operatively coupled to the second surface 236 of the first TEC 228 and may be configured to receive the absorbed heat from the first TEC 228 via the second surface 236 of the first TEC 228. Also, the first fan 232 is positioned proximate to the first heat sink 230 and may be configured to dissipate the heat from the first heat sink 230. In one example, the first fan 232 may be configured to blow cold air towards the first heat sink 230 to dissipate the heat from the first heat sink 230.

During operation of the ultrasound probe 202, various components, such as the transmit and receive circuitries and the beamformer in the probe 202 may generate heat in the probe 202. In one embodiment, wireless communication capabilities of these components and power supply from the batteries 216 to these components may also contribute to the heat generated in the probe 202. In one example, the heat generated within the probe 202 may have a value in the range from about 1 W to about 10 W. In another example, the heat may be generated within the probe 202 may have a value that is above 10 W.

Furthermore, the thermal unit 214 in the probe 202 absorbs this generated heat via the thermal management units 218. In one example, the PCM cartridges in the thermal unit 214 may be configured to absorb and store the heat via the thermal management units 218.

Moreover, when the ultrasound probe 202 is placed in the docking station 204, the induction unit 212 and the thermal unit 214 of the probe 202 may be respectively coupled to the first charging unit 220 and the first cooling unit 222 of the docking station 204. More specifically, the second wireless induction charging ring 226 of the first charging unit 220 may be magnetically coupled to the first wireless induction charging ring 213 of the induction unit 212 and configured to wirelessly charge the one or more batteries 216 in the probe 202.

Concurrently, the first TEC 228 in the first cooling unit 222 may be thermally coupled to the thermal unit 214 and configured to dissipate the heat generated in the probe 202. Particularly, the first surface 234 of the first TEC 228 in the first cooling unit 222 may contact the thermal unit 214 and may absorb the heat stored in the thermal unit 214. Further, the first heat sink 230 that is coupled to the first TEC 228 may receive this absorbed heat via the second surface 236 of the first TEC 228. Also, the first fan 232 that is coupled to or positioned proximate to the first heat sink 230 may be used to blow cold air to dissipate the heat from the first heat sink 230. Once the probe 202 is electrically charged and thermally cooled by the docking station 204, the probe 202 may be removed from the docking station 204 and may be used for scanning the patient/subject. In one embodiment, the thermal units 214 in the probe 202 may be replaced by a new set of thermal units. This aspect of replacing the thermal units 214 will be explained in greater detail with reference to FIGS. 3 and 4.

Thus, by employing the exemplary docking station 204, the probe 202 may be electrically charged, while simultaneously managing the thermal condition of the probe 202. Also, since the exemplary docking station 204 and probe 202 circumvent the need for increasing the surface area and/or overall size of the probe 202 for absorbing the heat in the probe 202, ergonomic and/or hygienic aspects of the probe 202 may be maintained or enhanced.

Figure 3:
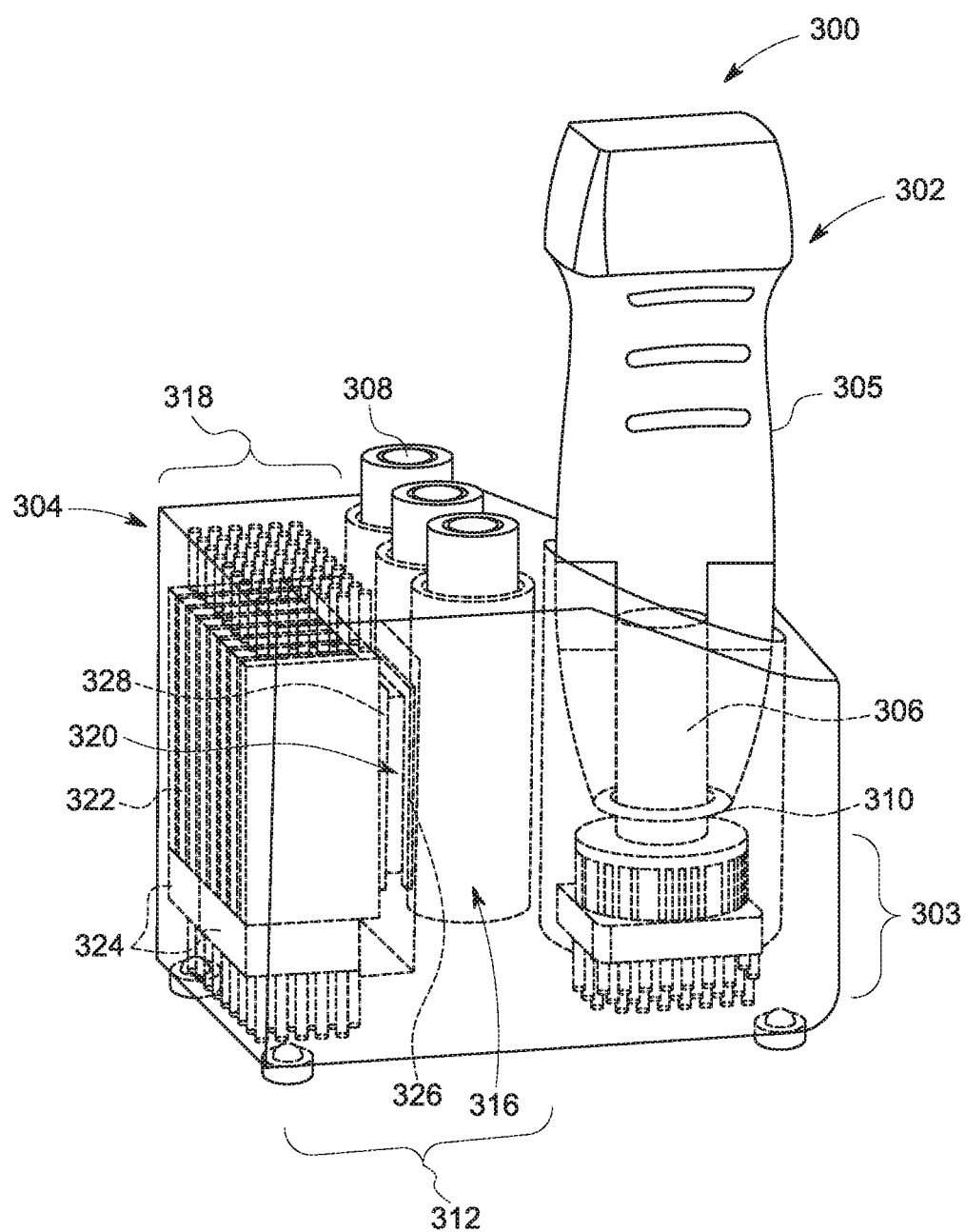
FIG. 3 is a diagrammatical representation of another embodiment of a docking station for electrically charging and thermally cooling the ultrasound probe, in accordance with aspects of the present specification.

Referring to FIG. 3, a diagrammatical representation 300 of another embodiment of an exemplary a docking station 304, in accordance with aspects of the present specification, is depicted. The docking station 304 may be configured to electrically charge an ultrasound probe 302 and concurrently manage a thermal condition of the ultrasound probe 302.

In the example of FIG. 3, the probe 302 includes a housing 305 having a thermal unit 306. The thermal unit 306 is used for absorbing heat generated in the probe 302. Additionally, in a presently contemplated configuration, the docking station 304 includes a first cooling unit 303 that is thermally coupled to the thermal unit 306 when the probe 302 is positioned in the docking station 304. Further, the first cooling unit 303 is used to dissipate the heat from the thermal unit 306.

It may be noted that the ultrasound probe 302 is similar to the ultrasound probe 202 of FIG. 2. However, in the embodiment of FIG. 3, the thermal unit 306 in the probe 302 may be replaced by a new thermal unit 308. By way of example, the thermal unit 306 in the probe 302 may be configured to absorb and store heat generated in the probe 302. In one example, once the thermal unit 306 has been in use for a determined period of time, the thermal unit 306 may be replaced by a new thermal unit 308. To this end, the probe 302 includes one or more ports that are used for replacing the thermal unit 306 in the probe 302 with the new thermal unit 308. It may be noted that the new thermal unit 308 has been cooled by the docking station 304. In one example, one of the ports that facilitate the replacement of the thermal units may be positioned at the bottom surface 310 of the probe 302. As the new thermal unit 308 is used to replace the thermal unit 306, the new thermal unit 308 may also be referred to as a replaceable thermal unit.

Furthermore, the docking station 304 is similar to the docking station 204 of FIG. 2. However, in the embodiment 300 of FIG. 3, the docking station 304 includes an additional section known as a bay assembly 312 for storing a plurality of replaceable thermal units 308. In one example, each of these replaceable thermal units 308 may be a phase change material (PCM) cartridge.

In the embodiment of FIG. 3, the bay assembly 312 includes a plurality of collars 316 and a second cooling unit 318. The collars 316 are configured to hold/house the replaceable thermal units 308. In one example, each of these collars 316 is a cylindrical housing that is used to hold/house one of the replaceable thermal units 308.

Further, the second cooling unit 318 is operatively coupled to the collars 316 and configured to dissipate heat from the replaceable thermal units 308. As depicted in FIG. 3, the second cooling unit 318 includes a second thermoelectric cooler (TEC) 320, a second heat sink 322, and a second fan 324. The second TEC 320 is positioned between the collars 316 and the second heat sink 322, while the second fan 324 is positioned below the second heat sink 322, as depicted in the embodiment of FIG. 3. In one embodiment, the second cooling unit 318 may include one or more additional fans disposed adjacent to the second fan 324 and below the second heat sink 322.

It may be noted that the in certain situations, the thermal units 308 may be a thermal unit that has been replaced. Hence, it may be desirable to cool the thermal unit by dissipating the heat stored in that thermal unit. Accordingly, the second TEC 320 is thermally coupled to the collars 316 to absorb the heat stored in the replaceable thermal units 308. More specifically, the second TEC 320 has a first surface 326 and a second surface 328. The first surface 326 is coupled to the collars 316 to absorb the heat stored in the replaceable thermal units 314. Further, the second heat sink 322 is coupled to the second surface 328 of the second TEC 320 and may be configured to receive the absorbed heat from the second TEC 320 via the second surface 328. Furthermore, the second fan 324 is operatively coupled to or positioned proximate to the second heat sink 322 and may be configured to dissipate the heat from the second heat sink 322. In one example, the second fan 324 may be configured to blow cold air towards the second heat sink 322 to dissipate the heat from the second heat sink 322.

Thus, by employing the docking station 304 having the bay assembly 312, the replaceable thermal units 308 may be thermally cooled and used to replace the thermal unit 306 in the probe 302. Also, in this example, since the thermal unit 306 in the probe 302 is replaced by one of the replaceable thermal units 308, the probe 302 need not be coupled to the docking station 302 for cooling. This in turn improves clinical workflow and patient throughput.

FIG. 4 is a diagrammatical representation 400 of yet another embodiment of an exemplary docking station 404, in accordance with aspects of the present specification. The docking station 404 may be configured to electrically charge an ultrasound probe 402 and concurrently manage a thermal condition of the ultrasound probe 402.

In the example of FIG. 4, the probe 402 includes a housing 405 having a sleeve 414 disposed therein. The sleeve 414 includes a replaceable cartridge 416 and a replaceable battery 418. The replaceable cartridge 416 may be similar to the thermal unit 214 of FIG. 2 and is used to absorb and store heat that is generated in the probe 402. Further, the replaceable battery 418 may be similar to the batteries 216 of FIG. 2 and are used to provide electrical power to other components in the probe 402. Also, the sleeve 414 may be replaceable by another sleeve 414 positioned in the bay assembly 406.

Additionally, in a presently contemplated configuration, the docking station 404 includes a first cooling unit 403 that is thermally coupled to the sleeve 414 when the probe 402 is positioned in the docking station 404. Further, the first cooling unit 403 is used to dissipate the heat from the replaceable cartridge 416 in the sleeve 414.

It may be noted that the docking station 404 is similar to the docking station 304 of FIG. 3. However, in the example of FIG. 4, the docking station 404 includes a bay assembly 406, which in turn includes a second charging unit 408 that is used to charge the replaceable batteries 418 in the sleeve 414.

In addition to the second charging unit 408, the bay assembly 406 includes a plurality of collars 410 and a second cooling unit 412. Further, each of these collars 410 is a cylindrical housing that is used to hold the sleeve 414. In the embodiment of FIG. 4, the replaceable cartridge 416 may be positioned such that the replaceable cartridge 416 is concentric with and surrounds the replaceable battery 418. In one example, the replaceable cartridge 416 may be a cylindrical housing that is used to hold/house the replaceable battery 418. In one embodiment, the replaceable cartridge 416 may be a PCM cartridge that is capable of absorbing and storing heat.

Further, the second cooling unit 412 may be thermally coupled to the collars 410 to absorb or dissipate heat from the replaceable cartridge 416 of the sleeve 414. Concurrently, the second charging unit 408 may be operatively coupled to each of the collars 410 to electrically charge the replaceable battery 418 in the sleeve 414. More specifically, the second charging unit 408 may be positioned at a bottom end 420 of each of the collars 410. Further, when the sleeve 414 is placed in the collars 410, the second charging unit 408 may be magnetically coupled with the replaceable battery 418 positioned within the sleeve 414. Also, the second charging unit 408 may wirelessly charge this replaceable battery 418. Moreover, upon electrically charging the replaceable battery 418 and thermally cooling the replaceable cartridge 416, the sleeve 414 may be used to replace a sleeve 414 positioned in the probe 402.

Thus, by employing the docking station 404 of FIG. 4, the replaceable batteries 418 are electrically charged and the replaceable cartridges 416 are thermally cooled. Also, as the sleeve 414 in the probe 402 is replaced by another sleeve 414 from the bay assembly 406, the probe 402 need not be coupled to the docking station 404 for electrically charging and thermally cooling the probe 402. Thus, use of the embodiment 400 of FIG. 4 facilitates enhanced clinical workflow and patient throughput.

FIG. 5 is a flow chart illustrating a method for electrically charging and managing a thermal condition of an ultrasound probe, in accordance with aspects of the present specification. The method is employed for maintaining desired electrical charge and thermal condition of the probe that is used for imaging a target volume, such as the chest, breast, and/or abdominal regions in a patient. For ease of understanding, the method 500 is described with reference to the components of FIGS. 1 and 2.

An ultrasound probe typically includes components that generate heat during operation. It is desirable to dissipate the heat from the probe to maintain a desired thermal condition of the probe. Additionally, it may also be desirable to maintain electrical charge in components, such as batteries in the probe to improve clinical workflow and patient throughput.

The method begins at step 502, where the ultrasound probe such as the probe 202 may be positioned in an exemplary docking station such as the docking station 204. Use of the method 500 aids in charging the probe 202 via the docking station 204, while also concurrently maintaining/managing a thermal condition of the probe 204.

Once the probe 202 is positioned in the docking station 204, the first charging unit 220 of the docking station 204 is magnetically coupled to the induction unit 212 of the ultrasound probe 202. This magnetic coupling of the induction unit 212 to the first charging unit 220 aids in charging at least one battery 216 in the ultrasound probe 202. Particularly, the induction unit 212 may include the first wireless induction charging ring 213 that is positioned at the bottom surface 210 of the housing 206 of the probe 202. Also, the first wireless induction charging ring 213 is electrically coupled to the battery 216 in the ultrasound probe 202. In a similar manner, the first charging unit 220 includes a second wireless induction charging ring 226. Further, when the probe 202 is positioned into the docking station 204, the second wireless induction charging ring 226 may be magnetically coupled to the first wireless induction charging ring 213 to electrically charge the at least one battery 216 in the probe 202.

In accordance with aspects of the present specification, the ultrasound probe 202 may be concurrently cooled while the battery 216 in the probe 202 is being charged. Accordingly, at step 504, the ultrasound probe 202 may be cooled by dissipating the heat in the probe 202. The heat generated by the various components in the probe 202 may be absorbed by the thermal management units 218. The thermal management units 218 in turn convey the heat to the thermal unit 214. The thermal unit 214 is configured to absorb the heat from the thermal management units 218 and store the heat.

Once the ultrasound probe 202 is positioned in the docking station 204, the first cooling unit 222 of the docking station 204 is thermally coupled to a thermal unit 214 of the ultrasound probe 202 to dissipate heat from the ultrasound probe 202. Particularly, the first cooling unit 222 includes a first thermoelectric cooler (TEC) 228, a first heat sink 230, and a first fan 232. The first TEC 228 is positioned on the first heat sink 230, while the first fan 232 is positioned below the first heat sink 230, as depicted in FIG. 2. Further, the first TEC 228 is thermally coupled to the thermal unit 214 of the probe 202 to absorb the heat stored in the thermal unit 214. In one example, the first TEC 228 may be concentrically positioned within the second wireless induction charging ring 226, as depicted in FIG. 2. In another example, the first TEC 228 may be a Peltier effect device that is capable of absorbing the heat from the thermal unit 214. Further, the absorbed heat in the first TEC 228 may be dissipated by using the first heat sink 230 and the first fan 232 in the first cooling unit 222.

The various embodiments of the exemplary system and method aid in electrically charging the probe while simultaneously managing the thermal condition of the probe. Also, the exemplary docking station circumvents the need for any increase in the surface area and/or overall size of the probe to dissipate the heat from the probe, thereby enhancing the ergonomic and/or hygienic aspects of the probe. Additionally, use of the various embodiments of the docking station and the probes provides enhanced clinical workflow and patient throughput. Also, by replacing the thermal unit and/or the battery in the probe with a corresponding new thermal unit and/or a new battery, user of the probe may be allowed to continue using the probe over an extended duration of time or at a higher performance without being thermally limited.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system comprising an ultrasound probe and a docking station, wherein the ultrasound probe comprises:
a housing with a top surface positioned at a first end of the probe and a bottom surface positioned at a second end of the probe opposite the first end;
a transducer array positioned proximate to the first end;
a beamformer, transmit circuitry, receive circuitry, a thermal unit, a battery and an induction unit disposed within the housing;
wherein the thermal unit is proximate to the second end and coupled to at least one of the transmit circuitry, the receive circuitry, and the beamformer;
wherein the induction unit is proximate to the second end and electrically coupled to the battery;
wherein the docking station is adapted to receive the ultrasound probe and comprises:
a cooling unit adapted to be thermally coupled to the thermal unit when the ultrasound probe is positioned in the docking station to thereby dissipate heat from the ultrasound probe; and
a charging unit adapted to be magnetically coupled to the induction unit when the ultrasound probe is positioned in the docking station to thereby charge the battery.

2. The system of claim 1, wherein the housing defines an elongated shape between the first end and the second end.

3. The system of claim 1, wherein the docking station defines a cavity for receiving the ultrasound probe.

4. The system of claim 3, wherein cavity is generally cylindrical and adapted to maintain the ultrasound probe in a generally vertical orientation when the ultrasound probe is positioned in the cavity.

5. The system of claim 4, wherein the portion of the docking station defining the cavity is lower on a first side than on a second side in a vertical direction.

6. The system of claim 3, wherein the docking station is adapted to maintain the ultrasound probe with the top surface positioned above the docking station when the bottom surface is positioned in the cavity.

7. The system of claim 6, wherein the docking station includes a slanted surface surrounding the cavity.

8. The system of claim 7, wherein more than 50% of the length of the ultrasound probe is positioned above the slanted surface of the docking station when the ultrasound probe is positioned in the cavity.

9. The system of claim 1, wherein the docketing station is attached to one of a console ultrasound system, a cart-based ultrasound system, and a portable ultrasound system.

10. The system of claim 1, wherein the thermal unit comprises a phase change material cartridge.

11. The system of claim 1, wherein the thermal unit is a cylindrical cartridge and the induction unit is disposed concentrically around the thermal unit.

12. The system of claim 1, wherein the induction unit comprises a first induction charging ring and the charging unit comprises a second induction charging ring, wherein the first induction charging ring is configured to magnetically couple to the second induction charging ring when the ultrasound probe is positioned in the docking station.

13. The system of claim 1, further comprising a display device attached to the docking station, wherein the display device is adapted to display one or more images generated from data acquired with the ultrasound probe.

14. The system of claim 1, further comprising a thermal management unit configured to couple the thermal unit to least one of the transmit circuitry, the receive circuitry, and the beamformer.

15. The system of claim 14, wherein the thermal management unit is a heat spreader.

16. The system of claim 14, wherein the thermal management unit is a heat pipe.

17. The system of claim 1, wherein the thermal unit in the ultrasound probe is configured to establish contact with the cooling unit when the ultrasound probe is positioned in the docking station.

18. The system of claim 1, wherein the cooling unit comprises a thermoelectric cooler.

19. The system of claim 18, wherein the cooling unit further comprises a fan configured to blow air over the thermoelectric cooler.

20. The system of claim 1, wherein the cooling unit comprises a fan.

* * * * *